(12) United States Patent
Swann et al.

(10) Patent No.: US 8,580,855 B2
(45) Date of Patent: *Nov. 12, 2013

(54) ACETAMINOPHEN / IBUPROFEN COMBINATIONS AND METHOD FOR THEIR USE

(75) Inventors: Jim Swann, Waterloo (CA); Peter Cummins, Guelph (CA)

(73) Assignee: McNeil-PPC, Inc., Skillman, NJ (US)

( * ) Notice: Subject to any disclaimer, the term of this patent is extended or adjusted under 35 U.S.C. 154(b) by 738 days.

This patent is subject to a terminal disclaimer.

(21) Appl. No.: 11/873,494

(22) Filed: Oct. 17, 2007

(65) Prior Publication Data

US 2008/0103206 A1    May 1, 2008

Related U.S. Application Data

(60) Provisional application No. 60/853,509, filed on Oct. 20, 2006.

(51) Int. Cl.
| | | |
|---|---|---|
| *A01N 37/10* | (2006.01) |
| *A01N 37/18* | (2006.01) |
| *A01N 37/44* | (2006.01) |
| *A01N 37/12* | (2006.01) |
| *A61K 31/19* | (2006.01) |
| *A61K 31/16* | (2006.01) |
| *A61K 31/195* | (2006.01) |

(52) U.S. Cl.
USPC ........... 514/570; 514/629; 514/567; 514/282; 514/357

(58) Field of Classification Search
USPC .................. 514/570, 576, 629, 567, 282, 357
See application file for complete search history.

(56) References Cited

U.S. PATENT DOCUMENTS

| | | |
|---|---|---|
| 4,173,626 A | 11/1979 | Dempski et al. |
| 4,543,370 A | 9/1985 | Porter |
| 4,643,894 A | 2/1987 | Porter |
| 4,683,256 A | 7/1987 | Porter |
| 4,725,441 A | 2/1988 | Porter |
| 4,762,702 A | 8/1988 | Gergely |
| 4,800,087 A | 1/1989 | Mehta |
| 4,802,924 A | 2/1989 | Woznicki |
| 4,820,524 A | 4/1989 | Berta |
| 4,828,841 A | 5/1989 | Porter |
| 4,851,226 A | 7/1989 | Julian et al. |
| 4,863,742 A | 9/1989 | Panoz et al. |
| 4,867,983 A | 9/1989 | Berta |
| 4,906,478 A | 3/1990 | Valentine |
| 4,966,771 A | 10/1990 | Berta |
| 4,980,170 A | 12/1990 | Schneider et al. |
| 4,984,240 A | 1/1991 | Keren-Zvi et al. |
| 5,013,557 A | 5/1991 | Tai |
| 5,075,114 A | 12/1991 | Roche |
| 5,089,270 A | 2/1992 | Hampton |
| 5,213,738 A | 5/1993 | Hampton |
| 5,275,822 A | 1/1994 | Valentine |
| 5,286,497 A | 2/1994 | Hendrickson et al. |
| 5,409,709 A | 4/1995 | Ozawa |
| 5,409,711 A | 4/1995 | Mapelli |
| 5,466,865 A | 11/1995 | Geyer |
| 5,489,436 A | 2/1996 | Hoy et al. |
| 5,630,871 A | 5/1997 | Jordan |
| 5,653,993 A | 8/1997 | Ghanta et al. |
| 5,658,589 A | 8/1997 | Parekh et al. |
| 5,912,013 A | 6/1999 | Rudnic et al. |
| 5,914,129 A | 6/1999 | Mauskop |
| 6,103,260 A | 8/2000 | Luber |
| 6,160,020 A | 12/2000 | Ohannesian et al. |
| 6,270,805 B1 | 8/2001 | Chen et al. |
| 6,274,162 B1 | 8/2001 | Steffenino |
| 6,322,819 B1 | 11/2001 | Burnside et al. |
| 6,432,442 B1 | 8/2002 | Buehler et al. |
| 6,440,983 B1 | 8/2002 | Frank-Kollman |
| 6,569,463 B2 | 5/2003 | Patel et al. |
| 6,627,212 B2 | 9/2003 | Uzunian et al. |
| 6,627,214 B1 | 9/2003 | Bunick |
| 2003/0068373 A1 | 4/2003 | Luber |
| 2003/0086973 A1 | 5/2003 | Sowden |
| 2003/0118654 A1 * | 6/2003 | B. Santos et al. ............. 424/486 |
| 2003/0124183 A1 | 7/2003 | Sowden |
| 2003/0219484 A1 | 11/2003 | Sowden |
| 2003/0235616 A1 | 12/2003 | Sowden |
| 2004/0156902 A1 | 8/2004 | Lee |

FOREIGN PATENT DOCUMENTS

| | | | |
|---|---|---|---|
| CA | 1336687 | * | 8/1995 |
| CA | 2411960 A1 | | 12/2001 |
| EP | 0 111 456 B1 | | 7/1989 |
| JP | 11158066 A | | 6/1999 |
| JP | 2003104903 A | | 4/2003 |

(Continued)

OTHER PUBLICATIONS

Meyer, J, Pharmacokinetics and Biopharmaceutics, 24, pp. 449-459, 1996.*

V. Dahl et al., Ibuprofen vs. Acetaminophen vs. Ibuprofen and Acetaminophen after Arthroscopically Assisted Anterior Cruciate Ligament Reconstruction. European Journal of Anesthesiology 2004; 21:471-475.

Chayna Sarkar et al., Analgesic use in Dentistry in a Tertiary Hospital in Western Nepal. Pharmacoepidemiology and Drug Safety 2004; 13:729-733.

Bhattachary S K et al., Potentiation of Gastric Toxicity of Ibuprofen by Paracetamol in the Rat.. Journal of Pharmacy and Pharmacology ( Jul. 1991); 43 (7) 520-1.

(Continued)

*Primary Examiner* — Sreeni Padmanabhan
*Assistant Examiner* — Uma Ramachandran
(74) *Attorney, Agent, or Firm* — Laura A. Donnelly

(57) ABSTRACT

A pharmaceutical dosage form is provided comprising a non-steroidal anti-inflammatory agent and acetaminophen, and methods for their use. In one embodiment, the dosage form is comprised of ibuprofen and acetaminophen as the sole pharmaceutically effective agents, wherein the ibuprofen and acetaminophen are in a weight ratio of about 12 parts:about 88 parts.

2 Claims, 1 Drawing Sheet

(56) References Cited

FOREIGN PATENT DOCUMENTS

| WO | WO 98/03179 A1 | 1/1998 |
|----|----------------|--------|
| WO | WO 9827931 A2 | 7/1998 |
| WO | WO 02/02081 A1 | 1/2002 |
| WO | WO 2004/096174 A1 | 11/2004 |

OTHER PUBLICATIONS

Lachman, et al., The Theory and Practice of Industrial Pharmacy, Chapter 11 (3rd ed. 1986).

Miranda et al, "Synergism between paracetamol and nonsteroidal anti-inflammatory drugs in experimental acute pain", *Pain*, Elsevier Science Publishers, Amsterdam, NL, vol. 121, No. 1-2 (Mar. 2006) pp. 22-28 (XP005330893).

Jung et al., "Onset of Analgesia and Analgesic Efficacy of Tramadol/Acetaminophen and Codeine/Acetaminophen/Ibuprofen in Acute Postoperative Pain: A Single-Center, Single-Dose, Randomized, Active-Controlled, Parallel-Group Study in a Dental Surgery Pain Model", *Clinical Therapeutics*, (2004) pp. 1037-1045, vol. 26, No. 7, Excerpta Medica, Inc. Publishers.

Carrive et al., "Changes in Formalin-Evoked Spinal Fos Expression and Nociceptive Behaviour After Oral Administration of Bufferin A (Aspirin) and L-5409709 (Ibuprofen + Caffeine + Paracetamol)", *Pain*, (Apr. 1997) pp. 253-266, vol. 70, Issue 2-3, Elsevier Science Publishers.

Fadl, et al., "Paracetamol (Acetaminophen) Esters of Some Non-Steroidal Anti-Inflammatory Carboxylic Acids As Mutual Prodrugs With Improved Therapeutic Index", *Inflammopharmacology* (1998) pp. 143-157, vol. 6, No. 2, Kluwer Academic Publishers.

Lickiss, "Approaching Cancer Pain Relief", *European Journal of Pain*, (2001) pp. 514, vol. 5, No. Suppl A, Elsevier Science Publishers.

Belikov, "High School", *Pharmaceutical Chemistry*, Moscow, 1993, vol. 1, pp. 43-47.

*Register of Pharmaceutical Agents of Russia, Encyclopedia of Drugs*, M, 2002, $9^{th}$ edition, pp. 345-346 and 654-655.

Stock et al. "S-ibuprofen versus ibuprofen-racemate. A randomized double-blind study in patients with rheumatoid arthritis", *Rheumatology Int.*, 1991, vol. 11(4-5), pp. 199-202.

USP 24, 2000 Version. pp. 19-20 and 856 (1999).

Pfaff, G. and Reynders, P., "Angle-dependent Optical Effects Deriving from Submicron Structures of Films and Pigmments". 99 Chem Rev. 1963-1981 (1999).

Seibel, K et al., " Comparison of Two Different Preparataions of Ibuprofen with Regard to the Time Course of their Analgesic Effect". 54(8) Arnzeimittel-Forschung 444-51 (2004).

Elizabeth Carbide Die Co., Inc. "The Elizabeth Companies Tablet Design Training Manual" p. 7 (McKeesport, Pa) 2003.

\* cited by examiner

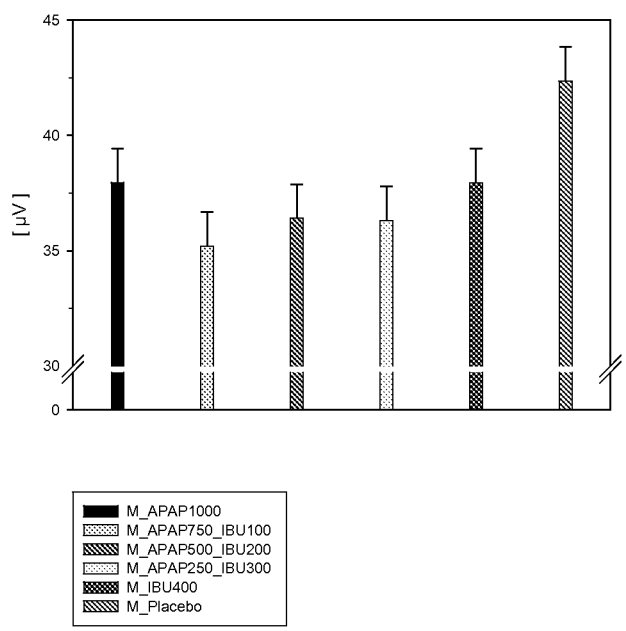

ACETAMINOPHEN / IBUPROFEN COMBINATIONS AND METHOD FOR THEIR USE

CROSS REFERENCE TO RELATED APPLICATION

This application is a claims domestic priority to provisional application No. 60/853,509 filed on Oct. 20, 2006, which is hereby incorporated in its entirety.

BACKGROUND OF THE INVENTION

1. Field of the Invention

This invention relates to dosage forms comprising non-steroidal anti-inflammatory agents and acetaminophen, and methods for their use. More specifically, this invention relates to dosage forms comprising synergistic combinations of ibuprofen and acetaminophen.

2. Description of the Related Art

Numerous antipyretic and analgesic products are frequently used and/or widely prescribed. One type of antipyretic/analgesic combination product includes salicylic acid derivatives such as aspirin with acetaminophen. Disadvantageously, dosage forms that include salicylic acid derivatives often cause gastric disorders. Gastric disorders such as, for example, nausea, gastralgia, and stomach discomfort, have also been associated with other non-steroidal anti-inflammatory-containing products, such as those containing ibuprofen, although to varying degrees and frequency.

One approach for suppressing these negative side effects has been the inclusion of an antacid into the dosage form. See, e.g., U.S. Pat. No. 5,409,709. Disadvantageously, the manufacture of such dosage forms has been complicated by the need to overcome the incompatibility of these ingredients.

In view of such side effects, it would therefore be beneficial to reduce the single dose or maximum daily dose of such active ingredients contained in dosage forms, while providing equal or better analgesic and/or antipyretic effect than the full single dose or full daily dose of either of the active ingredients contained therein.

It an object of the present invention to reduce the likelihood of any negative side effects that may be associated with the use of such analgesic or antipyretic ingredients by reducing the levels of such ingredients in the dosage form to an amount that is below the full single dose or full daily dose of each respective active ingredient alone, but which provides the desired or improved antipyretic and/or analgesic effects. Other objects, features and advantages of the invention will be apparent to those skilled in the art from the detailed description set forth below.

SUMMARY OF THE INVENTION

The present invention is directed to a preparation comprised of, consisting of, and/or consisting essentially of a) a first analgesic agent consisting of an effective amount of a non-steroidal, anti-inflammatory agent, which includes but is not limited to ibuprofen; pharmaceutically acceptable isomers, metabolites, polymorphs, and/or salts thereof; and mixtures thereof; and b) a second analgesic agent consisting of an effective amount of acetaminophen, pharmaceutically acceptable isomers, metabolites, polymorphs, and/or salts thereof; and mixtures thereof; wherein the first analgesic agent and the second analgesic agent are optionally the sole analgesic agents, and the weight ratio of the first analgesic agent (calculated as a racemic ibuprofen base) to the second analgesic agent (calculated as an acetaminophen base) is from about 5 parts to about 19 parts:about 81 parts to about 95 parts, and methods for its use as set forth in the claims.

BRIEF DESCRIPTION OF THE DRAWINGS

FIG. 1 graphically depicts the change in microvolts (uV) as an indication for the analgesic efficacy of each respective treatment studied in Example 1 using the LSEP methodology.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified. In addition, all ranges set forth herein are meant to include any combinations of values between the two endpoints, inclusively.

As used herein, the term "dosage form" applies to any ingestible forms, including confections. In one embodiment, dosage forms are solid, semi-solid, or liquid compositions designed to contain a specific pre-determined amount of a certain ingredient, for example an active ingredient as defined below. Suitable dosage forms may be pharmaceutical drug delivery systems, including those for oral administration, buccal administration, rectal administration, topical, transdermal, or mucosal delivery, or subcutaneous implants, or other implanted drug delivery systems; or compositions for delivering minerals, vitamins and other nutraceuticals, oral care agents, flavorants, and the like. In one embodiment, the dosage forms of the present invention are considered to be solid; however, they may contain liquid or semi-solid components. In another embodiment, the dosage form is an orally administered system for delivering a pharmaceutical active ingredient to the gastrointestinal tract of a human. In another embodiment the dosage form is a tablet or a simulated capsule like medicament, which may optionally contain a coating. In another embodiment the dosage form may have a portion comprised of the first analgesic agent and/or the second analgesic agent, whereby such agents are delivered in a sustained release manner. In yet another embodiment, the dosage form may contain active ingredients, other than the first analgesic agent and the second analgesic agent, for delivery via a sustained release manner. In yet another embodiment, the dosage form is an orally administered "placebo" system containing pharmaceutically inactive ingredients, and the dosage form is designed to have the same appearance as a particular pharmaceutically active dosage form, such as may be used for control purposes in clinical studies to test, for example, the safety and efficacy of a particular pharmaceutically active ingredient. In one embodiment, the dosage form contains all active ingredients within the same solid, semi-solid, or liquid forms. In another embodiment, the dosage form contains the active ingredients in one or more solid, semi-solid, or liquid forms.

As used herein, the term "preparation" or "dose" applies to the dosage form or forms necessary to be ingested by the patient in order for the patient to receive the desired amount of each active ingredient contained therein.

"Tablets," as used herein, refer to compressed or molded solid dosage forms of any shape or size.

As used herein, "injection molding" shall mean a process of forming a dosage form in a desired shape and size wherein a flowable material, which is in a fluid or flowable state form, enters a mold, then is solidified in the mold via a change in temperature (either positive or negative) before being removed therefrom. By contrast, "compression," as used herein, shall mean a process of forming a dosage form in a desired shape and size wherein a material is compacted into a tablet between the surfaces of punches via an increase in pressure before being removed therefrom.

As used herein, "racemic ibuprofen base" shall mean an equivalent mixture of the (R) and (S) stereoisomers of ibuprofen, more specifically, a mixture of about 50% (R)-ibuprofen and about 50% (S)-ibuprofen, and "acetaminophen base" shall mean acetaminophen calculated as a non-free acid or salt form of acetaminophen.

The present invention is directed to a dose or preparation comprising a first analgesic agent consisting of non-steroidal, anti-inflammatory agent ("NSAID(s)"), including but not limited to ibuprofen, and pharmaceutically acceptable isomers, metabolites, esters, polymorphs, and/or salts of such NSAIDs and mixtures thereof; and a second analgesic agent consisting of acetaminophen, pharmaceutically acceptable isomers, esters, metabolites, polymorphs, and/or salts thereof, and mixtures thereof, which are administered orally in a weight ratio of first analgesic agent (calculated in terms of an ibuprofen racemic base) to second analgesic agent (calculated in terms of an acetaminophen base) of about 5 parts to about 19 parts, i.e., e.g., from about 5 parts to about 12 parts:from about 81 parts to about 95 parts, i.e., e.g. from about 88 parts to about 95 parts. In one embodiment, the weight ratio of the first analgesic agent to the second analgesic agent is about 12 parts:about 88 parts, e.g., about 19 parts:about 81 parts or from about 5 parts:about 95 parts. In one optional embodiment, the first and second analgesic agents are the sole analgesic agents or the sole active agents in the dose or preparation.

In one embodiment, the dose or preparation of the present invention contains a first analgesic agent consisting of a pharmaceutically acceptable isomers, metabolites, esters, polymorphs, and/or salts of NSAID; and mixtures thereof; and a second analgesic agent consisting of acetaminophen pharmaceutically acceptable isomers, esters, metabolites, polymorphs, and/or salts thereof; and mixtures thereof, which are administered orally in a ratio of first analgesic agent (calculated as the percentage of the maximum adult analgesic dose of such NSAID base) to second analgesic agent (calculated as the percentage of the maximum adult analgesic dose of acetaminophen base) of about 12-37:about 87-62, i.e., e.g., from about 12.5-37.5:about 87.5-62.5. In one embodiment, the ratio of NSAID:APAP is about 25:about 75. Optionally, the first and second analgesic agents are the sole analgesic agents or the sole active agents in the dose or preparation.

The maximum adult analgesic single doses will vary depending upon the active ingredient selected. Such maximum adult analgesic doses for a non-prescription indication non exclusively include: 1) ketoprofen (25 mg): 2) naproxen (440 mg naproxen sodium, equivalent to 400 mg naproxen); 3) acetyl salicylic acid (aspirin) (1 g); and 4) APAP (1000 mg).

In one embodiment, an adult dose contains the first analgesic agent and the second analgesic agent in amounts effective for analgesic and antipyretic treatments, which typically comprises from about 50 mg to about 150 mg of ibuprofen (as calculated from the racemic ibuprofen base) and about 875 mg to about 625 mg of acetaminophen (as calculated from the acetaminophen base) per dose, i.e., e.g., about 100 mg of the first analgesic agent and about 750 mg of the second analgesic agent per dose The dose containing the first analgesic agent and the second analgesic agent can be administered to a person in need of analgesic relief at a frequency of about every two to eight hours.

Typically, oral doses of acetaminophen range from about 80 milligrams to about 1000 milligrams per dose, with a typical over the counter, non-prescription oral adult dose of about 1000 mg for maximum analgesic relief and with dosing every four to six hours up to a maximum of 4,000 mg per day. Oral doses of ibuprofen range from about 50 milligrams to about 800 milligrams, with a typical over the counter, non-prescription oral adult dose of about 400 mg for maximum analgesic relief and with dosing every four to six hours up to about 1200 mg per day. However, as a result of the synergistically improved antipyretic analgesic action of the dosage forms of the present invention, the oral doses of acetaminophen and ibuprofen used in accordance with the present invention are lower in amount relative to the amount of either analgesic used at their respective common dosage.

Examples of suitable non-steroidal anti-inflammatory drugs (NSAIDs) include, but are not limited to propionic acid derivatives: e.g. ibuprofen, naproxen, flurbiprofen, fenbufen, fenoprofen, indoprofen, ketoprofen, fluprofen, pirprofen, carprofen, oxaprozin, pranoprofen, suprofen, and the like; acetic acid derivatives: e.g. indomethacin, diclofenac, sulindac, tolmetin, and the like; fenamic acid derivatives: e.g. mefanamic acid, meclofenamic acid, flufenamic acid, and the like; biphenylcarbodylic acid derivatives: e.g. diflunisal, flufenisal, and the like; and oxicams, e.g. piroxicam, sudoxicam, isoxicam, meloxicam, and the like.

Examples of various forms of acetaminophen include suitable salts, alkaline metal, alkaline earth metal salts, amino acid esters of acetaminophen and free acids of acetaminophen as referenced in publication WO9827931A2. Examples of suitable pharmaceutically acceptable salts of acetaminophen include inorganic salts of acetaminophen, including: sodium, calcium, lithium, potassium, magnesium, cesium, ammonia, ferrous, zinc, manganous, aluminum, ferric, manganic, and the like, organic salts of acetaminophen with primary, secondary, tertiary and quaternary amines, substituted amines including naturally occurring substituted amines, cyclic amines and basic ion exchange resins, triethylamine, tripropylamine, 2-dimethylaminoethanol, 2-diethylaminoethanol, lysine, arginine, histidine, caffeine, procain, N-ethylpiperidine, hydrabamine, choline, betaine, ethylenediamine, glucosamine, methylglycamine, theobromine, pruines, piperazine, piperidine, polyamine resins and the like, and mixtures thereof.

Examples of suitable pharmaceutically acceptable salts of ibuprofen include ibuprofen lysinate, dexibuprofen lysinate, and sodium and potassium salts of ibuprofen. Other examples of pharmaceutically acceptable salts of ibuprofen include salts with alkaline earth metals, such as magnesium, aluminum, iron, zinc, copper, nickel or cobalt, and amino acid salts, particularly the basic amino acid salts such as lysine or arginine. Examples of suitable forms of ibuprofen include, but are not limited to racemic and individual purified forms of (S) ibuprofen and (R)-ibuprofen isomers, including (S)-ibuprofen-(S)-lysine, (S)-ibuprofen-(R)-lysine, (R)-ibuprofen-(S)-lysine and (R)-ibuprofen-(R)-lysine and combinations thereof.

Suitable dosage forms include solids or liquids. Solid forms include tablets, capsules, liquid-filled soft gelatin capsules, liquid filled hard gelatin capsules, semi-solid or emulsion filled soft gelatin capsules, semi-solid or emulsion filled hard gelatin capsules, powders, sachets and the like. Suitable liquids include suspensions, solutions, emulsions and the like.

The dose (e.g. amount) of the first analgesic agent and the second analgesic agent used in the present invention may be administered in one dosage form, or in a plurality of dosage forms. In one embodiment, the dose may be comprised of one dosage form that contains the first analgesic agent and a second dosage form that contains the second analgesic agent. In another embodiment, the dose may be comprised of one dosage form containing both the first and second analgesic agents. In yet another embodiment, the dose may be comprised of a plurality of dosage forms, each of which contains both the first and second analgesic agents.

In one embodiment, the dose may include other analgesic agents that include, but are not limited to, cox-2 inhibitors such as celecoxib, valdecoxib, meloxicam; codeine; oxycodone; hydrocodone; tramadol; diclofenac; and combinations thereof.

In one embodiment, the dose may contain one or more active ingredient other than an analgesic. "Active ingredients" or "active agents" as used herein, include, for example, pharmaceuticals, minerals, vitamins and other nutraceuticals, oral care agents, flavorants and mixtures thereof. Suitable pharmaceuticals include anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable oral care agents include breath fresheners, tooth whiteners, antimicrobial agents, tooth mineralizers, tooth decay inhibitors, topical anesthetics, mucoprotectants, and the like.

Suitable flavorants include menthol, peppermint, mint flavors, fruit flavors, chocolate, vanilla, bubblegum flavors, coffee flavors, liqueur flavors and combinations and the like.

Suitable acidulants include malic acid, fumaric acid, citric acid, acetic acid, benzoic acid, ascorbic acid, and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotidine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for H. pylori, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

In one embodiment of the invention, the active ingredient may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment of the invention, the active ingredient may be selected from pseudoephedrine, phenylpropanolamine, phenylephrine, chlorpheniramine, dextromethorphan, diphenhydramine, astemizole, terfenadine, fexofenadine, loratadine, desloratidine, doxilamine, norastemizole, cetirizine, guaifenesin, benzocaine, menthol, modafinil, nifedipene, sidenefil, mixtures thereof and pharmaceutically acceptable salts, esters, isomers, and mixtures thereof.

Examples of suitable polydimethylsiloxanes, which include, but are not limited to dimethicone and simethicone, are those disclosed in U.S. Pat. Nos. 4,906,478; 5,275,822; and 6,103,260. As used herein, the term "simethicone" refers to the broader class of polydimethylsiloxanes, including but not limited to simethicone and dimethicone.

In one embodiment, the dose may include active ingredients including, but not limited to methocarbamol; dextromethorphan; phenylephrine; pseudoephedrine; doxylamine; guaifenesin; chlorpheniramine; antacids such as calcium carbonate and the like; simethicone; cyclobenzaprine; chloroxazone; glucosamine; chondroitin; and combinations thereof.

In one embodiment, the dosage form is substantially free of antacids. As used herein, "substantially free of antacids" shall mean that the dosage form contains less than about 0.05 parts by weight of antacid based upon 1 part by weight of the total amount of the first and second analgesic agent.

The optional active ingredient or ingredients are present in the dosage form(s) of the present invention in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors must be considered, as known in the art. In one embodiment, the dosage form comprises at least about 85 weight percent of the optional active ingredient, first analgesic agent, and second analgesic agent.

The first analgesic agent, second analgesic agent, and optional active ingredient or ingredients may be present in the dosage form(s) in a variety of formats. For example, these components may be dispersed at the molecular level, e.g. melted or dissolved, within the dosage form, or may be in the form of particles, which in turn may be coated or uncoated. Particles may be present in the shell and/or the core of the dosage form. If the active ingredient is in form of particles, the particles (whether coated or uncoated) typically have an average particle size of about 1 micron to about 2000 microns. In one embodiment, such particles are crystals having an average particle size of about 1 micron to about 300 microns, or about 10 microns to about 120 microns. In yet another embodiment, the particles are granules or pellets having an average particle size of about 50 microns to about 2000 microns, e.g. from about 50 microns to about 1000 microns or from about 100 microns to about 800 microns.

In certain embodiments in which modified release of the active ingredient is desired, the first analgesic agent, second analgesic agent, and optional active ingredient may optionally be coated with a known release-modifying coating. This advantageously provides an additional tool for modifying the release profile of active ingredient from the dosage form. For example, the dosage form may contain coated particles of one or more active ingredients, in which the particle coating confers a release modifying function, as is well known in the art.

Examples of suitable release modifying coatings for particles are described in U.S. Pat. Nos. 4,173,626; 4,863,742; 4,980,170; 4,984,240; 5,286,497; 5,912,013; 6,270,805; and 6,322,819. Commercially available modified release active ingredients may also be employed. For example, acetaminophen particles, which are encapsulated with release-modifying polymers by a coaccervation process, may be used in the present invention. Such coaccervation-encapsulated acetaminophen is commercially available from, for example, Eurand America, Inc. or Circa Inc.

If the first analgesic agent, second analgesic agent, or optional active ingredient has an objectionable taste, and the dosage form is intended to be chewed or disintegrated in the mouth prior to swallowing, these components may be coated with a taste masking coating, as known in the art. Examples of suitable taste masking coatings are described in, for example, U.S. Pat. Nos. 4,851,226; 5,075,114; and 5,489,436. Commercially available taste masked active ingredients may also be employed. For example, acetaminophen particles, which are encapsulated with ethylcellulose or other polymers by a coaccervation process, may be used in the present invention. Such coaccervation-encapsulated acetaminophen is commercially available from Eurand America, Inc. or Circa Inc. Additional suitable methods for applying taste-masked coatings are well known in the art and include but are not limited to fluid bed coating, complex coaccervation, spray drying, and spray congealing as disclosed in, for example, U.S. Pat. Nos. 4,851,226, 5,653,993, 5,013,557, and 6,569,463, respectively.

The first analgesic agent, second analgesic agent, and optional active ingredient or ingredients are typically capable of dissolution upon contact with a fluid such as water, stomach acid, intestinal fluid or the like. In one embodiment, the dissolution characteristics of these components meet USP specifications for immediate release tablets containing the active ingredient. In embodiments in which it is desired for these components to be absorbed into the systemic circulation of an animal, the first analgesic agent, second analgesic agent, and optional active ingredient or ingredient should be capable of dissolution upon contact with a fluid such as water, gastric fluid, intestinal fluid or the like. In one embodiment, the dissolution characteristics of these components meet USP specifications for immediate release tablets containing the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999). In another embodiment, the dissolution characteristics of the first analgesic agent, second analgesic agent, and optional active ingredient or ingredient may be modified: e.g. controlled, sustained, extended, retarded, prolonged, or delayed.

In one embodiment, the core may also optionally comprise a sub-core (which may also be referred to as an "insert"), which may be made by any method, for example compression or molding, and which may optionally contain the first analgesic agent, second analgesic agent, and/or optional active ingredient or ingredients.

The core (or substrate) may be any solid or semi-solid form. As used herein, "substrate" refers to a surface or underlying support, upon which another substance resides or acts, and "core" refers to a material, which is at least partially enveloped or surrounded by another material. In one embodiment, the core comprises a solid, for example, the core may be a compressed or molded tablet, hard or soft capsule, suppository, or a confectionery form such as a lozenge, nougat, caramel, fondant, or fat based composition. In certain other embodiments, the core may be in the form of a semi-solid or a liquid in the finished dosage form.

The core of the present invention may be prepared by any suitable method, including for example compression and molding, and depending on the method by which it is made, typically comprises active ingredient and a variety of excipients, i.e., inactive ingredients which may be useful for conferring desired physical properties to the dosage core.

In embodiments wherein the core is a compressed dosage form, for example, a compressed tablet, the core may be obtained from a compressed powder. The powder may contain an active ingredient, and optionally comprise various excipients, such as binders, disintegrants, lubricants, fillers and the like, as is conventional, or the powder may comprise other particulate material of a medicinal or non-medicinal nature, such as inactive placebo blends for tableting, confectionery blends, and the like. One particular formulation comprises active ingredient, as an excipient, a plastically deforming compressible material, and optionally other excipients, such as disintegrants and lubricants and is described in more detail in United States Patent Application Publication No. 20030068373. During compression, the plastically deforming compressible material assumes the shape of the microrelief from the upper and/or lower punch surface.

Suitable plastically deforming compressible materials for these embodiments include but are not limited to: microcrystalline cellulose, waxes, fats, mono- and di-glycerides, derivatives and mixtures thereof, and the like. In certain embodiments, wherein the plastically deforming compressible material is later caused to melt and be absorbed into the tablet, the plastically deforming compressible material may be selected from low-melting plastically deforming compressible materials, such as plastically deforming compressible powdered waxes, such as shellac wax and microcrystalline wax, polyethylene glycol, and mixtures thereof.

Suitable fillers include, but are not limited to, water-soluble compressible carbohydrates such as sugars, which include dextrose, sucrose, isomaltalose, fructose, maltose, and lactose, polydextrose, sugar-alcohols, which include mannitol, sorbitol, isomalt, maltitol, xylitol, erythritol, starch hydrolysates, which include dextrins, and maltodextrins, and the like, water insoluble plastically deforming materials such as microcrystalline cellulose or other cellulosic derivatives, water-insoluble brittle fracture materials such as dicalcium phosphate, tricalcium phosphate and the like and mixtures thereof.

Suitable binders include, but are not limited to, dry binders such as polyvinyl pyrrolidone, hydroxypropylmethylcellulose, and the like; wet binders such as water-soluble polymers, including hydrocolloids such as alginates, agar, guar gum, locust bean, carrageenan, tara, gum arabic, tragacanth, pectin, xanthan, gellan, maltodextrin, galactomannan, pusstulan, pullulan, laminarin, scleroglucan, gum arabic, inulin, pectin, whelan, rhamsan, zooglan, methylan, chitin, cyclodextrin, chitosan, polyvinyl pyrrolidone, cellulosics, starches, and the like; and derivatives and mixtures thereof.

Suitable disintegrants include, but are not limited to, sodium starch glycolate, cross-linked polyvinylpyrrolidone, cross-linked carboxymethylcellulose, starches, microcrystalline cellulose, and the like.

Suitable lubricants include, but are not limited to, long chain fatty acids and their salts, such as magnesium stearate and stearic acid, talc, and waxes.

Suitable glidants include, but are not limited to, colloidal silicon dioxide, and the like.

In embodiments in which the core is prepared via compression, the core may also incorporate pharmaceutically acceptable adjuvants, including, but not limited to preservatives, high intensity sweeteners such as aspartame, acesulfame potassium, cyclamate, saccharin, sucralose, and the like; and other sweeteners such as dihydroalcones, glycyrrhizin, Monellin™, stevioside, Talin™, and the like; flavors, antioxidants, surfactants, and coloring agents.

In certain embodiments the core is prepared as a multilayer tablet optionally surrounded by a shell portion. In one embodiment the core is prepared as a bi-layer tablet wherein one analgesic is included in one layer and the second analgesic is included in a second layer.

In one embodiment, the dosage form has 2 or more core portions separated by a shell layer. In one embodiment the first core portion contains the first analgesic agent and the second core portion contains the second analgesic agent such as the type of dosage form referenced in US patent application US20030235616A1.

In yet another embodiment of the invention, the dosage forms of this invention comprise a core made from a blend of powders having an average particle size of about 50 microns to about 500 microns. In one embodiment, the active ingredient has an average particle size of about 50 microns to about 500 microns. In another embodiment, at least one excipient has an average particle size of about 50 microns to about 500 microns, e.g. about 100 to about 500 microns. In one such embodiment, a major excipient, i.e. an excipient comprising at least 50% by weight of the core, has an average particle size of about 50 microns to about 500 microns, e.g. about 100 to about 500 microns. Particles in this size range are particularly useful for direct compression processes.

In one embodiment of the invention, the core may be a directly compressed tablet made from a powder that is substantially free of water soluble polymeric binders and hydrated polymers. This composition is advantageous for maintaining an immediate release dissolution profile, minimizing processing and material costs, and providing for optimal physical and chemical stability of the dosage form.

In embodiments in which the core is prepared by direct compression, the materials comprising the core, e.g. the active ingredient or ingredients and excipients, may be blended together, for example as dry powders, and fed into a cavity of an apparatus that applies pressure to form a core. Any suitable compacting apparatus may be used, including for example a roller compactor such as a chilsonator or drop roller; or a conventional tablet press. In one embodiment, the core may be formed by compaction using a rotary tablet press as known in the art. In general, a metered volume of powder is filled into a die cavity of the rotary tablet press, and the cavity rotates as part of a "die table" from the filling position to a compaction position. At the compaction position, the powder is compacted between an upper and a lower punch, then the resulting tablet is pushed from the die cavity by the lower punch. Advantageously, the direct compression process enables the minimization or elimination of water-soluble, non-saccharide polymeric binders such as polyvinyl pyrrolidone, alginates, hydroxypropyl cellulose, hydroxypropylmethylcellulose, hydroxyethylcellulose, and the like, which could have a negative effect on dissolution.

In another embodiment, the core may be prepared by the compression methods and apparatus described in United States Patent Application Publication No. 20040156902. Specifically, the core may be made using a rotary compression module comprising a fill zone, insertion zone, compression zone, ejection zone, and purge zone in a single apparatus having a double row die construction as shown in FIG. 6 of United States Patent Application Publication No. 20040156902. The dies of the compression module may then be filled using the assistance of a vacuum, with filters located in or near each die. The purge zone of the compression module includes an optional powder recovery system to recover excess powder from the filters and return the powder to the dies.

In another embodiment, the core may be prepared by a wet-granulation method, in which the active ingredient or ingredients, appropriate excipients, and a solution or dispersion of a wet binder (e.g. an aqueous cooked starch paste, or solution of polyvinyl pyrrolidone) may be mixed and granulated. Suitable apparatus for wet granulation include low shear, e.g. planetary mixers, high shear mixers, and fluid beds, including rotary fluid beds. The resulting granulated material may then be dried, and optionally dry-blended with further ingredients, e.g. adjuvants and/or excipients such as, for example, lubricants, colorants, and the like. The final dry blend is then suitable for compression by the methods described in the previous paragraph.

Methods for direct compression and wet granulation processes are known in the art, and are described in detail in, for example, Lachman, et al., *The Theory and Practice of Industrial Pharmacy*, Chapter 11 (3rd ed. 1986).

The shell may be applied via any means known in the art such as, for example, spray coating as disclosed in, U.S. Pat. Nos. 4,683,256; 4,543,370; 4,643,894; 4,828,841; 4,725,441; 4,802,924; 5,630,871; and 6,274,162; dip coating as disclosed in, U.S. Pat. Nos. 5,089,270; 5,213,738; 4,820,524; 4,867,983; and 4,966,771; or injection molding as disclosed in, US application 2003-0219484 A1.

In one embodiment, the shell or core may also be prepared by thermal setting injection molding using the method and apparatus in which the mold is maintained at approximately a constant temperature as described in United States Patent Application Publication No. 20030124183. In this embodiment, the first portion or core may be formed by injecting a starting material in flowable form into a molding chamber. The starting material may comprise an active ingredient and a thermally responsive material, which is introduced to the mold at a temperature above the glass transition temperature or set temperature of the thermally responsive material but below the decomposition temperature of the active ingredient. The starting material is then cooled and solidified in the molding chamber into a desired shaped form (i.e. the shape of the mold). The starting material, when at a temperature that is greater than its glass transition temperature or its set temperature, is sufficiently flowable to be easily injected or pumped into the molding chamber.

As used herein, "thermally responsive material" shall include materials that, as the temperature applied to the material is increased, become softer, and as the temperature applied is reduced, the materials conversely becomes harder and have reduced flow. In the case of gels, "set temperature" shall mean the temperature at which a gel-forming material rapidly solidifies through the gelation process.

In another embodiment, the shell or core may be prepared by thermal cycle injection molding using the method and apparatus, in which the mold is cycled between at least two temperatures, as described in United States Patent Application Publication No. 20030086973. In this embodiment, the first portion or core may be formed by injecting a starting material in flowable form into a heated molding chamber. The starting material may comprise an active ingredient and a thermoplastic material at a temperature above the glass transition temperature or set temperature of the thermally responsive material but below the decomposition temperature of the active ingredient. The starting material is then cooled and solidified in the molding chamber into a desired shaped form (i.e. the shape of the mold).

According to either of these molding methods, the starting material must be in flowable form. For example, it may comprise solid particles suspended in a molten matrix such as a polymer matrix. Alternatively, the starting material may be completely molten or in the form of a paste. In one embodiment, the starting material may comprise an active ingredient dissolved in a molten material. Alternatively, the starting material may be made by dissolving a solid in a solvent, which solvent may then be evaporated from the starting material after it has been molded.

The starting material may comprise any edible material which is desirable to incorporate into a shaped form, including active ingredients such as those active ingredients previously described with respect to the core, nutritionals, vitamins, minerals, flavors, sweeteners, and the like. Typically, the starting material comprises an active ingredient and a thermally responsive material. The thermally responsive material may be any edible material that is flowable at a temperature between about 37° C. and about 250° C., and that is a solid or semi-solid at a temperature between about −10° C. and about 35° C. When it is in the fluid or flowable state, the flowable starting material may comprise a dissolved or molten component, and optionally a solvent such as for example water or organic solvents, or combinations thereof. The solvent may be partially or substantially removed by drying.

Suitable flowable, starting materials include, but are not limited to those thermally responsive materials such as film forming polymers, gelling polymers, hydrocolloids, low melting hydrophobic materials such as fats and waxes, noncrystallizable carbohydrates, and the like.

Examples of suitable thermally responsive materials include, but are not limited to water-soluble polymers such as polyalkylene glycols, polyethylene oxides and derivatives, and sucrose-fatty acid esters; fats such as cocoa butter, hydrogenated vegetable oil such as palm kernel oil, cottonseed oil, sunflower oil, and soybean oil; free fatty acids and their salts; mono- di- and triglycerides, phospholipids, waxes such as carnuba wax, spermaceti wax, beeswax, candelilla wax, shellac wax, microcrystalline wax, and paraffin wax; fat-containing mixtures such as chocolate; sugar in the form of an amorphous glass such as that used to make hard candy forms, sugar in a supersaturated solution such as that used to make fondant forms; carbohydrates such as sugar-alcohols (for example, sorbitol, maltitol, mannitol, xylitol and erythritol), or thermoplastic starch; and low-moisture polymer solutions such as mixtures of gelatin and other hydrocolloids at water contents up to about 30%, such as for example those used to make "gummi" confection forms. In one embodiment, the thermally responsive material is a blend of fats and mono- and diglycerides.

In one embodiment of the invention, the flowable materials may comprise a film former such as a cellulose ether, e.g. hydroxypropylmethylcellulose or a modified starch, e.g. waxy maize starch; optionally a polycarbohydrate, e.g. maltodextrin; optionally a hydrocolloid, e.g. xanthan gum or carrageenan, or a sugar, e.g. sucrose; and optionally a plasticizer such as polyethylene glycol, propylene glycol, vegetable oils such as castor oil, glycerin, and mixtures thereof.

Any film former known in the art is also suitable for use as a thermally responsive material. Examples of suitable film formers include, but are not limited to, polyvinylalcohol (PVA), polyvinylpyrrolidone (PVP), hydroxypropyl starch, hydroxyethyl starch, pullulan, methylethyl starch, carboxymethyl starch, methylcellulose, hydroxypropylcellulose (HPC), hydroxyethylmethylcellulose (HEMC), hydroxypropylmethylcellulose (HPMC), hydroxybutylmethylcellulose (HBMC), hydroxyethylethylcellulose (HEEC), hydroxyethylhydroxypropylmethyl cellulose (HEMPMC), methacrylic acid and methacrylate ester copolymers, polyethylene oxide and polyvinylpyrrolidone copolymers, gelatin, proteins such as whey protein, coaggulatable proteins such as albumin, casein, and casein isolates, soy protein and soy protein isolates, pre-gelatinized starches, and polymers and derivatives and mixtures thereof.

One suitable hydroxypropylmethylcellulose compound is HPMC 2910, which is a cellulose ether having a degree of substitution of about 1.9 and a hydroxypropyl molar substitution of 0.23, and containing, based upon the total weight of the compound, from about 29% to about 30% methoxyl groups and from about 7% to about 12% hydroxylpropyl groups. HPMC 2910 is commercially available from the Dow Chemical Company under the tradename, "METHOCEL E." METHOCEL E5, which is one grade of HPMC-2910 suitable for use in the present invention, has a viscosity of about 4 to 6 cps (4 to 6 millipascal-seconds) at 20° C. in a 2% aqueous solution as determined by a Ubbelohde viscometer. Similarly, METHOCEL E6, which is another grade of HPMC-2910 suitable for use in the present invention, has a viscosity of about 5 to 7 cps (5 to 7 millipascal-seconds) at 20° C. in a 2% aqueous solution as determined by a Ubbelohde viscometer. METHOCEL E15, which is another grade of HPMC-2910 suitable for use in the present invention, has a viscosity of about 15000 cps (15 millipascal-seconds) at 20° C. in a 2% aqueous solution as determined by a Ubbelohde viscometer. As used herein, "degree of substitution" shall mean the average number of substituent groups attached to a anhydroglucose ring, and "hydroxypropyl molar substitution" shall mean the number of moles of hydroxypropyl per mole anhydroglucose.

As used herein, "modified starches" include starches that have been modified by crosslinking, chemically modified for improved stability, or physically modified for improved solubility properties. As used herein, "pre-gelatinized starches" or "instantized starches" refers to modified starches that have been pre-wetted, then dried to enhance their cold-water solubility. Suitable modified starches are commercially available from several suppliers such as, for example, A.E. Staley Manufacturing Company, and National Starch & Chemical Company. One suitable modified starch includes the pre-gelatinized waxy maize derivative starches that are commercially available from National Starch & Chemical Company, such as PURITY GUM 59, and derivatives, copolymers, and mixtures thereof. Such waxy maize starches typically contain, based upon the total weight of the starch, from about 0 percent to about 18 percent of amylose and from about 100% to about 88% of amylopectin.

Suitable tapioca dextrins include those available from National Starch & Chemical Company under the tradenames "CRYSTAL GUM" or "K-4484," and derivatives thereof such as modified food starch derived from tapioca, which is available from National Starch and Chemical under the tradename, "PURITY GUM 40," and copolymers and mixtures thereof.

Examples of suitable hydrocolloids (also referred to herein as gelling polymers) include but are not limited to alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, chitosan, and derivatives and mixtures thereof.

Suitable xanthan gums include those available from C.P. Kelco Company under the tradenames, "KELTROL 1000," "XANTROL 180," or "K9B310."

Thermoplastic materials that can be molded and shaped when heated are suitable for use as the thermally responsive material, and include both water soluble and water insoluble polymers that are generally linear, not crosslinked, nor strongly hydrogen bonded to adjacent polymer chains. Examples of suitable thermoplastic materials include: chemically modified cellulose derivatives such as hydroxypropyl cellulose (HPC), hydroxypropylmethyl cellulose (HPMC), methyl cellulose (MC), cellulose acetate (CA), ethyl cellulose (EC), cellulose acetate butyrate (CAB), cellulose propionate; vinyl polymers such as polyvinyl alcohol (PVA) and polyvinyl pyrrolidone (PVP); thermoplastic starch; thermoplastic gelatin, natural and chemically modified proteins such as gelatin, soy protein isolates, whey protein, myofibrillar proteins, and the milk derived caseinate proteins; and derivatives and combinations thereof.

Any plasticizer known in the pharmaceutical art is suitable for use in the flowable material, and may include, but not be limited to polyethylene glycol; glycerin; sorbitol; triethyl citrate; tribuyl citrate; dibutyl sebecate; vegetable oils such as castor oil; surfactants such as polysorbates, sodium lauryl sulfates, and dioctyl-sodium sulfosuccinates; propylene glycol; mono acetate of glycerol; diacetate of glycerol; triacetate of glycerol; natural gums and mixtures thereof. In solutions containing a cellulose ether film former, an optional plasticizer may be present in an amount, based upon the total weight of the solution, from about 0% to about 40%.

Any thickener known in the art may optionally be added to the thermally responsive material. Additional suitable thickeners include, but are not limited to, cyclodextrin, crystallizable carbohydrates, and the like, and derivatives and combinations thereof. Suitable crystallizable carbohydrates include the monosaccharides and the oligosaccharides. Of the monosaccharides, the aldohexoses e.g., the D and L isomers of allose, altrose, glucose, mannose, gulose, idose, galactose, talose, and the ketohexoses e.g., the D and L isomers of fructose and sorbose along with their hydrogenated analogs: e.g., glucitol (sorbitol), and mannitol are preferred. Of the oligosaccharides, the 1,2-disaccharides sucrose and trehalose, the 1,4-disaccharides maltose, lactose, and cellobiose, and the 1,6-disaccharides gentiobiose and melibiose, as well as the trisaccharide raffinose are preferred along with the isomerized form of sucrose known as isomaltulose and its hydrogenated analog isomalt. Other hydrogenated forms of reducing disaccharides (such as maltose and lactose), for example, maltitol and lactitol are also preferred. Additionally, the hydrogenated forms of the aldopentoses: e.g., D and L ribose, arabinose, xylose, and lyxose and the hydrogenated forms of the aldotetroses: e.g., D and L erythrose and threose are suitable and are exemplified by xylitol and erythritol, respectively.

The flowable material may optionally comprise adjuvants or excipients, which may comprise up to about 20% by weight of the flowable material. Examples of suitable adjuvants or excipients include detackifiers, humectants, surfactants, anti-foaming agents, colorants, flavorants, sweeteners, opacifiers, and the like. In one embodiment, the flowable material comprises less than 5% humectants, or alternately is substantially free of humectants, such as glycerin, sorbitol, maltitol, xylitol, or propylene glycol. Humectants have traditionally been included in pre-formed films employed in enrobing processes, such as that disclosed in U.S. Pat. Nos. 5,146,730 and 5,459,983 to ensure adequate flexibility or plasticity and bondability of the film during processing. Humectants function by binding water and retaining it in the film. Pre-formed films used in enrobing processes can typically comprise up to 45% water. Disadvantageously, the presence of humectant prolongs the drying process, and can adversely affect the stability of the finished dosage form.

In another embodiment, the core may be a hollow or evacuated core. For example, the core may be an empty capsule shell. Alternatively, a hollow core may be prepared for example by injection molding or shell molding. In one such method, flowable material is injected into a mold cavity, then cavity is brought to a temperature at which the outer surface of the core (which is in contact with the mold) begins to solidify or set. The excess flowable material from the center of the core is then withdrawn from the mold using suitable means, for example a piston pump. In another such method, an empty capsule is used as a sub-core, and a coating layer is formed thereon by methods known in the art such as, for example, spray-coating, dip-coating, injection cycle molding as described in, for example, United States Patent Application Publication No. 20030086973. In certain embodiments of the invention, the core may further comprise any of the aforementioned subcoatings applied by any method known in the art, for example spraying, compression, or molding. In certain other embodiments of the invention, the core may be substantially free of a subcoating.

In another embodiment of the invention, the core contains at least in part one or more inserts. The inserts can be made in any shape or size. For instance, irregularly shaped inserts can be made, that is shapes having no more than one axis of symmetry. Cylindrically shaped inserts may also be made. The insert may be made using conventional techniques such as panning, compression, or molding. In one embodiment, the insert is prepared using the injection molding methods and apparatus as described herein.

In one embodiment of the invention, the insert may have an average diameter from about 100 to about 1000 microns. In another embodiment of this invention, the insert may have an average diameter or thickness from about 10% to about 90% of the diameter or thickness of the core. In yet another embodiment of this invention, the core may comprise a plurality of inserts.

In another embodiment, the insert may have an average diameter, length, or thickness greater than about 90% of the diameter or thickness of the core, for example the insert may have an average length greater than about 100% of the thickness of the core.

In another embodiment of the invention, the core, the insert (if employed), the inlaid portion or any combination thereof may comprise a microelectronic device (e.g. an electronic "chip") which may be used as an active component or to control, for example, the rate of release of active ingredients within the core or insert in response to an input signal.

The core may be in a variety of different shapes and densities. In one embodiment, the core may have a density of about 0.7 g/cc to about 3.0 g/cc. With respect to different shapes, in one embodiment the core may be in the shape of a truncated cone. In other embodiments the core may be shaped as a polyhedron, such as a cube, pyramid, prism, or the like; or may have the geometry of a space figure with some non-flat faces, such as a cone, cylinder, sphere, torus, or the like. Exemplary core shapes which may be employed include tablet shapes formed from compression tooling shapes described by "The Elizabeth Companies Tablet Design Training Manual" (Elizabeth Carbide Die Co., Inc., p. 7 (McKeesport, Pa.) (incorporated herein by reference) as follows (the tablet shape corresponds inversely to the shape of the compression tooling):

Shallow Concave.
Standard Concave.
Deep Concave.
Extra Deep Concave.
Modified Ball Concave.
Standard Concave Bisect.
Standard Concave Double Bisect.
Standard Concave European Bisect.
Standard Concave Partial Bisect.
Double Radius.
Bevel & Concave.
Flat Plain.
Flat-Faced-Beveled Edge (F.F.B.E.).
F.F.B.E. Bisect.
F.F.B.E. Double Bisect.
Ring.
Dimple.
Ellipse.
Oval.
Capsule.
Rectangle.
Square.
Triangle.
Hexagon.
Pentagon.
Octagon.
Diamond.
Arrowhead.
Bullet.
Barrel.
Half Moon.
Shield.
Heart.
Almond.
House/Home Plate.
Parallelogram.
Trapezoid.
Figure 8/Bar Bell.
Bow Tie.
Uneven Triangle.

The core or sub-core may optionally be at least partially covered by a compressed, molded, or sprayed sub-coating. However, in another embodiment, the core may be substantially free of the subcoating, i.e., there is no subcoating located between the outer surface of the core and the inner surface of the shell. Any composition suitable for film-coating a tablet may be used as a subcoating according to the present invention. Examples of suitable subcoatings include, but are not limited to, those disclosed in, for example, U.S. Pat. Nos. 4,683,256, 4,543,370, 4,643,894, 4,828,841; 4,725, 441; 4,802,924; 5,630,871; and 6,274,162.

Additional suitable subcoatings may include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates, pigments, and opacifiers.

In one embodiment, the subcoating may be comprised of, based upon the total weight of subcoating, from about 2 percent to about 8 percent, e.g. from about 4 percent to about 6 percent, of a water-soluble cellulose ether; and from about 0.1 percent to about 1 percent of castor oil, as disclosed in U.S. Pat. No. 5,658,589. In another embodiment, the subcoating may be comprised of, based upon the total weight of the subcoating, from about 20 percent to about 50 percent, e.g., from about 25 percent to about 40 percent of HPMC; from about 45 percent to about 75 percent, e.g., from about 50 percent to about 70 percent of maltodextrin; and from about 1 percent to about 10 percent, e.g., from about 5 percent to about 10 percent of PEG 400.

In one embodiment, the subcoating and/or the top coating may comprise an effect pigment that acts to maximize the reflectance of the core. Examples of suitable effect pigments include, but are not limited to, platy titanium dioxide, such as that disclosed in U.S. Pat. No. 6,627,212; and transition metal oxide coated platy mica such as that commercially available from EMD Chemicals Inc. under the tradename, "CANDURIN." See also Pfaff, G. and Reynders, P., "*Angle-dependent Optical Effects Deriving from Submicron Structures of Films and Pigments,*" 99 Chem. Rev. 1963-1981 (1999). In embodiments wherein the dosage form contains a subcoating, the dosage form may contain, based upon the total weight of the dosage form, from about 1 percent to about 5 percent of the subcoating.

In one embodiment of the invention, only the core comprises the first analgesic agent, the second analgesic agent, and the optional active ingredients. In another embodiment of this invention, only the second portion of the shell comprises such ingredients. In yet another embodiment of this invention, only the insert comprises such ingredients. In yet another embodiment of this invention, both the core and the first shell portion and/or the second shell portion comprise such ingredients. In yet another embodiment of this invention, one or more of the core, the first shell portion, the second shell portion, or the insert comprises such ingredients. Optionally, any of the coatings may further comprise such ingredients.

The first and second portions of the coating may be made from the aforementioned thermally responsive materials, which for food and pharmaceutical uses may be any material that has been approved for use in foods and pharmaceuticals and can be molded, including for example, film formers, low-melting hydrophobic materials, gelling polymers, thickeners, plasticizers, adjuvants, and excipients.

In one embodiment, at least one of the first or second portions comprises at least about 50%, e.g. at least about 80%, or at least about 90% of a material selected from film formers, gelling polymers, low-melting hydrophobic materials, non-crystallizable sugars or sugar alcohols, and mixtures thereof. In another embodiment, at least one of the first or second portions comprises at least about 50%, e.g. at least about 80% or at least about 90% of a material selected from film formers, gelling polymers, low-melting hydrophobic materials, and mixtures thereof.

In one embodiment of the invention, the flowable material comprises gelatin as a gelling polymer. Gelatin is a natural, thermogelling polymer. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67% gelatin gel that has been held at 10° C. for 17 hours.

In one embodiment, the flowable material is an aqueous solution comprising 20% 275 Bloom pork skin gelatin, 20% 250 Bloom Bone Gelatin, and approximately 60% water. In one embodiment, at least one of the first portions or second portions comprises gelatin having a Bloom of about 150 to about 300, e.g., from about 200 to about 275.

In another embodiment of the invention, at least one of the first portions or second portions of the dosage form comprises at least about 80%, e.g. at least about 90%, of a material selected from film formers, gelling polymers (hydrocolloids), thermoplastic materials, low-melting hydrophobic materials, non-crystallizable sugars, and mixtures thereof.

In one embodiment, the dosage form contains a core having two faces and a belly band therebetween, and a shell having a thickness from about 100 microns to about 400 microns that substantially covers at least one face surface. The other face surface may be compositionally and/or visually different from the shell. The shell may contain, based upon the total weight of said shell, less than about 50 percent crystallizable sugar.

An optional top coating may be applied to the outer core surface of the dosage form via any of the above-described coating application methods such as, for example, spraying, molding, or dipping, and at a temperature below the melting temperature of the core material. In embodiments wherein the core is a compressed powder blend, such temperature may typically range from about 5° C. to about 120° C.

Suitable polymers for inclusion in top coatings include polyvinylalcohol (PVA); water soluble polycarbohydrates such as hydroxypropyl starch, hydroxyethyl starch, pullulan, methylethyl starch, carboxymethyl starch, pre-gelatinized starches, and film-forming modified starches; water swellable cellulose derivatives such as hydroxypropyl cellulose (HPC), hydroxypropylmethyl cellulose (HPMC), methyl cellulose (MC), hydroxyethylmethylcellulose (HEMC), hydroxybutylmethylcellulose (HBMC), hydroxyethylethylcellulose (HEEC), and hydroxyethylhydroxypropylmethyl cellulose (HEMPMC); water soluble copolymers such as methacrylic acid and methacrylate ester copolymers, polyvinyl alcohol and polyethylene glycol copolymers, polyethylene oxide and polyvinylpyrrolidone copolymers; polyvinylpyrrolidone and polyvinylacetate copolymers; and derivatives and combinations thereof. Suitable film-forming water insoluble polymers for inclusion in top coatings include for example ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof. Suitable film-forming pH-dependent polymers for inclusion in top-coatings include enteric cellulose derivatives, such as for example hydroxypropyl methylcellulose phthalate, hydroxypropyl methylcellulose acetate succinate, cellulose acetate phthalate; natural resins, such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename, "EUDRAGIT S;" and poly(methacrylic acid, methyl methacrylate) 1:1, which is commercially available from Rohm Pharma GmbH under the tradename, EUDRAGIT L; poly(butyl methacrylate (dimethylaminoethyl)methacrylate, methyl methacrylate), which is commercially available from Rohm Pharma GmbH under the tradename, "EUDRAGIT E;" and the like, and derivatives, salts, copolymers, and combinations thereof.

In one embodiment, a top coating includes those coatings having a high rigidity, i.e., e.g., those coatings having a yield value sufficient to prevent deformation of the randomized pattern when exposed to normal manufacturing, handling, shipping, storage, and usage conditions. Suitable top coatings having high rigidity include film formers, such as for example, the high tensile strength film-formers well known in the art. Examples of suitable high tensile strength film-formers include, but are not limited to methacrylic acid and methacrylate ester copolymers; polyvinylpyrrolidone; cellulose acetate; hydroxypropylmethylcellulose ("HPMC"), polyethylene oxide and polyvinylalcohol, which is commercially available from BASF under the tradename, "Kollicoat IR"; ethylcellulose; polyvinyl alcohols; and copolymers and mixtures thereof.

In one embodiment, the top coatings may include the water-soluble high rigidity film formers selected from HPMC, polyvinylpyrrolidone, the aminoalkyl-methacrylate copolymers marketed under the trademark, "EUDRAGIT E," and copolymers and mixtures thereof.

In embodiments wherein high clarity is of particular concern, the top coatings may include the high clarity high-rigidity film formers selected from the acrylates such as the aminoalkyl-methacrylate copolymers marketed under the trademark, "EUDRAGIT E," polyvinylpyrrolidone, cellulose acetate, polyethylene oxide and polyvinylalcohol, ethylcellulose, and polyvinyl alcohol shellac.

In general, the thickness of the top coating may range from about 50 microns to about 200 microns, and the rigidity of the top coating will increase as the thickness is increased.

The top coating may be applied via any means known in the art such as, for example, spray coating as disclosed in, U.S. Pat. Nos. 4,683,256, 4,543,370, 4,643,894, 4,828,841, 4,725,441, 4,802,924, 5,630,871, and 6,274,162; dip coating as disclosed in, U.S. Pat. Nos. 5,089,270; 5,213,738; 4,820,524; 4,867,983; and 4,966,771; or injection molding as disclosed in, US application 2003-0219484 A1.

Beneficially, as a result of the administration of the first analgesic agent and the second analgesic agent of the present invention, we have unexpectedly found that the analgesic effect of such a dose is superior to that obtained if one were to administer each analgesic at their respective maximum dosage amounts. We have also unexpectedly found that, when ibuprofen and acetaminophen are administered to a human in need thereof in accordance with the regimens set forth herein the total amount of analgesic used in each respective dose was also significantly lower than if one were administered each analgesic at their respective common dosage amounts. Further, the dosage forms of the present invention may also be made with, components, apparatus and processes that are not only economical to use, but also are compatible with current production techniques.

This invention will be further illustrated by the following examples, which are not meant to limit the invention in any way. Although this invention has been illustrated by reference to specific embodiments, it will be apparent to those skilled in the art that various changes and modifications may be made which clearly fall within the scope of this invention.

EXAMPLES

Example 1

Procedure for Analyzing Analgesic Properties Using Laser Somatosensory Evoked Potentials (LSEPs)

General Timing of Study: Each subject was treated on six different treatment days in a randomized, placebo-controlled, double-blind six sequence cross-over study, with each treatment being a different dosage combination of acetaminophen ("APAP") and ibuprofen ("IBU") administered in a random order. The total duration of the study per subject was about 46 days. The washout period between the six treatment days was about 7 days. About 2 to 14 days before receiving the first treatment, each subject participated in a one-day, pre-study examination visit.

On each treatment day, each subject stayed for approximately 7 hours at the treatment center, and followed the schedule set forth below in Table A:

TABLE A

Treatment Schedule for Analgesic Dosages

| Time | Action |
| --- | --- |
| −2.25 hours | A pulsed $CO_2$ laser was used to induce a painful stimulus on normal skin as a "warm-up" procedure. The intensity of the laser stimulus required to reach the pain threshold on normal skin was determined individually for each subject during the pre-study examination visit. The laser intensity for each painful stimulus remained constant for each individual patient throughout the study. |
| −2.05 hours | A pulsed $CO_2$ laser was used to induce a painful stimulus on normal skin to obtain baseline measures of pain |
| −2.00 hours | About a 4" × 4" square of skin on each patient ("Treated Area") was exposed to UV(B) light from an ultraviolet lamp at a dose of 2 times the minimal erythema dose ("MED"). The MED was determined during the pre-study visit by exposing a 4" × 4" square of skin to UV light until a dosage of light was found that induced a minimal erythema, e.g., the lowest dose that produced a red edge around the treated skin. |
| −1.00 hours | A pulsed $CO_2$ laser was used to induce a painful stimulus on the Treated Area as a "wind-up" procedure.* |
| −0.15 hours | A pulsed $CO_2$ laser was used to induce a painful stimulus on the Treated Area as a second "wind-up" procedure.* |
| 0 hours | Each subject ingested the ibuprofen/acetaminophen dosage for the day with 150 mL of water. |
| 35 minutes | A pulsed $CO_2$ laser was used to induce a painful stimulus on the UV irradiated skin.* |
| 60 minutes | A pulsed $CO_2$ laser was used to induce a painful stimulus on the UV irradiated skin.* |
| 120 minutes | A pulsed $CO_2$ laser was used to induce a painful stimulus on the UV irradiated skin.* |
| 180 minutes | A pulsed $CO_2$ laser was used to induce a painful stimulus on the UV irradiated skin.* |
| 240 minutes | A pulsed $CO_2$ laser was used to induce a painful stimulus on the UV irradiated skin.* |

*LSEP pain data was also collected at this time
*VAS pain data was also collected at this time (for second application)

Method of Pain Induction: A pulsed CO2 laser, which is commercially available from Synrad, Inc., under the tradename, "Synrad Infrared Gas Laser," model E48-/-26W was used to induce painful stimuli in the desired skin location.

Evaluation of Pain Relief: Laser induced somatosensory evoked potentials (LSEPs), which served as an objective-quantitative measurement of pain, were generating using Vertex-EEG readings collected using a MUX800/UBV800 Multiplexer and universal bio-amplifier with integrated 15 Hz-impedance measurement, both of which are commercially available from Rimkus Medizintechnik. Twelve artifact free EEG-sections of 3 second duration were averaged in two steps: (1.) 3×4 original sweeps; and (2.) 3×1 averaged sweeps, digitally filtered (Gaussian phase-free software filter on the basis of a Fast Fourier Transform (FFT), with ranges from 1.0 Hz to 12.5 Hz (first step) and 1.5 to 10.0 Hz (second step)). Means were analyzed for a time window of 600 ms after laser stimulation to identify and measure the components of the evoked potentials (latencies and amplitudes). The N1 and P2 components, which are the pain related components of the EEG-signal, were derived as described above and analyzed in accordance with the procedure set forth in Schaffler K., et al., "Analgesic effects of low-dose intravenous orphenadrine in the state of capsaicin hyperalgesia. A randomised, placebo-controlled, double-blind cross-over study using laser somatosensory evoked potentials obtained from capsaicin-irritated skin in healthy volunteers," 54(10) Arzneimittel-Forschung. 673-9 (2004). The N1-P2-peak-to peak amplitudes as well as the amplitudes of the individual N1 and P2 components were determined from the Vertex-EEG reading, and the correlated pain response was thereby determined in accordance with the procedure generally set forth in Seibel, K., et al., "Comparison of Two Different Preparations of Ibuprofen with Regard to the Time Course of their Analgesic Effect," 54(8) Arnzei-mittel-Forschung 444-51 (2004). The LSEP recording at hour −2:05 served as baseline (=t0). Drug induced analgesia was reflected by an amplitude reduction versus control or comparator treatment.

According to this procedure, a change in LSEP amplitude of about 1.0 to 3.0 pV was previously determined to be generally sufficient to allow for statistically significant discrimination between, for example, a given active agent vs. placebo, vs. other active agents, and/or vs. different dosages of the same active agent. An amplitude difference in the LSEP that exceeds about 2.0-2.5 pV (in peak-to-peak (PtP) amplitude) and >about 1.00-1.25 pV (for the single N1- and P2-components) was defined as clinically relevant.

Example 2

Determination of Efficacy Using LSEP Methodology

The procedure set forth in Example 1 was independently performed on 24 subjects in a randomized, placebo-controlled, double-blind 6 sequence cross-over study. The six ibuprofen/acetaminophen treatments administered on the treatment days consisted of two white caplets and 4 red tablets comprised of the doses set forth in Table B:

TABLE B

Dosages of Acetaminophen and Ibuprofen

| Treatment | Acetaminophen (mg) | Ibuprofen (mg)+ |
| --- | --- | --- |
| 1 | 1000* | 0 |
| 2 | 750*** | 100 |
| 3 | 500* | 200 |
| 4 | 250** | 300 |
| 5 | 0 | 400 |
| 6 | 0 - placebo++ | 0 - placebo |

*The Acetaminophen 500 mg dose samples were the "TYLENOL ®" acetaminophen 500 mg film coated tablets, which were manufactured in the McNeil Consumer Healthcare production facilities in Guelph, Ontario, Canada. Similarly, the Acetaminophen 1000 mg Dose Sample included two of these 500 mg tablets.
**The Acetaminophen 250 mg dose samples were produced in accordance with the procedure set forth in Example 3.
***The Acetaminophen 750 mg dose sample used the above 500 mg "TYLENOL" tablet and the 250 mg acetaminophen tablet produced in accordance with the procedure set forth in Example 3.
+The Ibuprofen dose Samples included one or more of the "MOTRIN ®" ibuprofen 100 mg caplets manufactured by McNeil Consumer Healthcare in Fort Washington, PA, USA.
++The placebo samples were produced in accordance with the procedure set forth in Example 4.

The results of the study are presented in Table C below and in FIG. 1. The impact of different treatments on peak-to-peak LSEP amplitudes over the treatment period is demonstrated in FIG. 1, with the APAP750 mg/IBU100 mg treatment showing the greatest overall reduction versus the placebo treatment arm, and accordingly the greatest analgesic effect.

Table C shows the statistical results of all pair-wise comparisons of treatments within the study. Treatment A and Treatment B displayed identified the specific treatment comparisons completed. P-Values of less than 0.05 identified statistically significant differences between the comparison treatments.

TABLE C

Pair-Wise Comparison of Treatments

| Treatment A | Treatment B | Estimate* | Standard Error | DF | tValue | p-value |
|---|---|---|---|---|---|---|
| APAP 750 mg + IBU 100 mg | Placebo | −7.1507 | 1.0402 | 569 | −6.87 | <.0001 |
| APAP 250 mg + IBU 300 mg | Placebo | −6.0437 | 1.0542 | 569 | −5.73 | <.0001 |
| APAP 500 mg + IBU 200 mg | Placebo | −5.9409 | 1.0424 | 569 | −5.70 | <.0001 |
| IBU 400 mg | Placebo | −4.4134 | 1.0383 | 569 | −4.25 | <.0001 |
| APAP 1000 mg | Placebo | −4.4020 | 1.0540 | 569 | −4.18 | <.0001 |
| APAP 750 mg + IBU 100 mg | IBU400 | −2.7374 | 1.0397 | 569 | −2.63 | 0.0087 |
| APAP 1000 mg | APAP750 + IBU100 | 2.7487 | 1.0516 | 569 | 2.61 | 0.0092 |
| APAP 1000 mg | APAP250 + IBU300 | 1.6417 | 1.0575 | 569 | 1.55 | 0.1211 |
| APAP 250 mg + IBU 300 mg | IBU400 | −1.6304 | 1.0525 | 569 | −1.55 | 0.1219 |
| APAP 500 mg + IBU 200 mg | IBU400 | −1.5276 | 1.0415 | 569 | −1.47 | 0.1430 |
| APAP 1000 mg | APAP500 + IBU200 | 1.5389 | 1.0518 | 569 | 1.46 | 0.1440 |
| APAP 500 mg + IBU 200 mg | APAP750 + IBU100 | 1.2098 | 1.0386 | 569 | 1.16 | 0.2446 |
| APAP 150 mg + IBU 300 mg | APAP750 + IBU100 | 1.1070 | 1.0450 | 569 | 1.06 | 0.2899 |
| APAP 250 mg + IBU 300 mg | APAP500 + IBU200 | −0.1028 | 1.0422 | 569 | −0.10 | 0.9215 |
| APAP 1000 mg | IBU400 | 0.01133 | 1.0534 | 569 | 0.01 | 0.9914 |

*"Estimate" is a term generated in the statistical program, which reflects the difference between Treatment A and Treatment B. This difference is then used to determine the T-value and P-value.

This Example showed that, with respect to peak-to-peak LSEP measurements, the APAP 1000 mg, IBU 400 mg and all combinations of APAP/IBU treatments showed significantly lower amplitudes and therefore were significantly more effective analgesics than the placebo. This is also evidenced in FIG. 1 by the lower peak-to-peak amplitudes recorded for these treatments relative to that recorded for the placebo. In addition, FIG. 1 and Table C showed that the APAP 750 mg+IBU 100 mg treatment was significantly more effective than 1000 mg APAP treatment or 400 mg IBU treatment, respectively, which unexpectedly evidenced that this combination is more effective in treating pain than a full dose of either active agent alone.

The calculations for the determination of appropriate ratios for the acetaminophen dose to the ibuprofen dose are outlined in Table D. For example, to calculate the percent (%) of APAP of total weight (as calculated in terms of acetaminophen base), the dose (mg) is calculated using the percent (%) as calculated in terms of a maximum adult analgesic dose of such acetaminophen base:

e.g. *APAP* Low mg Range @ 62.5%=1000 mg Maximum single dose×(62.5/100)=625 mg

To calculate the percent (%) of APAP of total weight (which is calculated in terms of acetaminophen base), the APAP low mg range is divided by the total weight of the doses of ibuprofen and APAP combined and multiplied by a factor of 100.

e.g. % of Total weight of *APAP*=625 mg *APAP*/775 mg Total Weight×100=81%

TABLE D

| APAP 75% of therapeutic Dose + IBU 25% of therapeutic dose as target ||||| 
|---|---|---|---|---|
| Active Analgesic Ingredient | Max Dose (mg) | Target mg @75% of max | Low Range mg @ 62.5% of max | High Range mg at 87.5% of max |
| APAP | 1000 | 750 | 625 | 875 |
| | Max Dose (mg) | Target mg @25% of max | High Range mg at 37.5% of max | Low Range mg @ 12.5% of max |
| Ibuprofen | 400 | 100 | 150 | 50 |
| Total Weight (mg) | n/a | 850 | 775 | 925 |
| % APAP of Total Weight | | 88% | 81% | 95% |
| % Ibuprofen of Total Weight | | 12% | 19% | 5% |

Example 3

Production of 250 g Acetaminophen Tablets

Tablets having the formulation set forth in Table E below were manufactured as follows:

TABLE E

Formulation of 250 mg acetaminophen caplet

| Material | Manufacturer | Mg/Caplet | % Target/Caplet |
|---|---|---|---|
| Acetaminophen | Mallinckrodt | 250.0 | 81.97 |
| Powdered Cellulose | Fibre Sales & Devel. | 20.4 | 6.69 |

TABLE E-continued

Formulation of 250 mg acetaminophen caplet

| Material | Manufacturer | Mg/Caplet | % Target/Caplet |
|---|---|---|---|
| Pregelatinized Starch | National Starch | 5.0 | 1.64 |
| Sodium Starch Glycolate | DMV International | 5.0 | 1.64 |
| Modified Starch | Grain Processing Group | 23.0 | 7.54 |
| Magnesium Stearate | Mallinckrodt | 1.6 | 0.52 |

Example 3(a)

Preparation of Starch Granulating Solution Paste 217.0 kg of purified water were added to a granulator starch kettle for an Aeromatic S9 fluid bed granulator. After 46,000 g of modified starch were added thereto and mixed for at least 5 minutes, the resulting starch paste was heated to 86° C. 43.0 kg of purified water were then added to the granulator starch paste kettle and mixed. The resulting starch granulating solution paste was allowed to cool to a temperature of not more than 77° C.

Example 3(b)

Granulation Processing 500 kg Acetaminophen, 40.8 kg powdered cellulose, 10 kg of pregelatinized starch and 10 kg of sodium starch glycolate were added to the bowl of an Aeromatic S9 fluid bed granulator. The starch granulating solution paste prepared in Example 3(a) was added thereto via an inlet air temperature of about 63° C. to about 86° C., an inlet air volume of not more than 6000 cfm, an atomization air pressure of 6 bar, and a spray rate of about 3.5 kg/min to about 4.5 kg/min. The target peak moisture during processing was 10%.

After the granulation was dried using an inlet air temperature of about 78° C. to about 93° C. and an inlet air volume of not more than 6000 cfm, the endpoint moisture content of the granulation was about 1.8% to about 2.3%.

Example 3(c)

Blending 3.2 kg of Magnesium stearate was added to the granulation prepared in Example 3(b) and blended coarsely using a paddle. After the granulation was screened through a Co-Mill fitted with a 0.094 inch screen, the milled granulation was then blended in a Tote-Bin blender for 110 revolutions.

Example 3(d)

Compression of Tablets

Using the blend prepared in Examples 3(a)-3(c) above, tablets were compressed using a Manesty BB4 rotary tablet press fitted with round concave tablets tooling at a weight of 205 mg and a hardness of 8.5 kilopounds (kp).

Example 3(e)

Preparation of Tablet Coating 16.52 g of sucralose which was commercially available from Tate & Lyle, Inc., was added to 990.0 g of purified water with mixing with a bench top mixer at a speed of 50 r.p.m. for about 13 minutes until the resulting mixture was clear and without visible crystals. 401.2 g of Opadry II Red Y-22-15056 was then added thereto with mixing for about 100 minutes.

Example 3(f)

Coating of Tablet Cores 10.0 kg of the 250 mg acetaminophen tablet cores produced in accordance with Example 3(e) were placed into an Accela Cota tablet coater and processed with an air volume of about 190 cfm to about 210 cfm, a pan speed of about 10 rpm to about 16 rpm, an atomizing air pressure of 4 bar, and a spray rate of 30-45 ml/minute.

The tablet cores were then sprayed, and the product bed was jogged until an exhaust temperature of 45° C. was obtained. After the product bed was allowed to cool to a temperature not more than 40° C., 0.52 g of carnuba wax was added thereto, and the pan was rotated slowly for 3 minutes.

Example 4

Preparation of Placebo Tablets

Placebo tablets were manufactured using the formulation set forth below in Table F as follows:

TABLE F

Formulation of Placebo Tablets

| Material | Manufacturer | Mg/tablet | % |
|---|---|---|---|
| Sugar, Compressible White | Domino Specialty | 500.41 | 81.50 |
| Microcrystalline Cellulose | Ming Tai | 110.52 | 18.00 |
| Magnesium Stearate | Mallinckrodt | 3.07 | 0.50 |

Example 4(a)

Blending and Compression 24,450.0 g of white compressible sugar, 5400.0 g of microcrystalline cellulose and 150.0 g of magnesium stearate were passed through a CoMill, a conical mill used to achieving uniform size reduction, sieving, deagglomeration, dispersion and mixing, equipped with a 0.094-inch screen. The material was then loaded in a tote bin blender available from Tote Systems International, LP, and blended end over end for 110 revolutions. The resulting blend was then compressed on a Manesty BB4 rotary tablet press fitted with $^{29}/_{64}$ inch round concave tablet tooling at a hardness of 11 kp in order to yield tablets having a weight of 614.0 mg.

Example 4(b)

Tablet Coating

After 1990.0 g of purified water were added to a suitable mixing container, 6.52 g of Sucralose were added thereto while mixing with a bench top mixer for about 13 minutes until the mixture was clear and no visible crystals were present. 401.2 g of Opadry II Red Y-22-15056 were then added to the solution with mixing for about 100 minutes. 10.0 kg of placebo tablet cores produced in accordance with Example 4(a) were then placed into an Accela Cota tablet coater and processed with an air volume of 190-210 cfm, a pan speed of 10-16 rpm, atomizing air pressure of 4 bar, and spray rate of 30-45 ml/minute for about 62 minutes or until the tablets incurred a weight gain of about 3.3%.

After spraying, the product bed was then jogged until an exhaust temperature of 45° C. was obtained. After the product bed was allowed to cool to a temperature not more than 40° C., 0.52 g of carnuba wax was added thereto, and the pan was rotated slowly for 3 minutes.

We claim:

1. A method for mitigating and/or treating pain and/or inflammation, comprising:
    providing an oral dose to a subject in need thereof, wherein the oral dose comprises:
    a) a first analgesic agent selected from the group consisting of ibuprofen; one or more pharmaceutically acceptable isomers, polymorphs, and/or salts of ibuprofen; and mixtures thereof; and
    b) a second analgesic agent selected from the group consisting of acetaminophen, one or more pharmaceutically acceptable isomers, polymorphs, and/or salts of acetaminophen; and mixtures thereof;
    wherein the weight ratio of the first analgesic agent to the second analgesic agent is about 1 part to about 7.5 parts; and
    wherein the first analgesic agent and the second analgesic agent are the sole active ingredients in the dose.

2. The method of claim 1, wherein the dose comprises about 100 milligrams of said first analgesic agent and about 750 milligrams of said second analgesic agent.

* * * * *